United States Patent
Dixon (12) 
(10) Patent No.: US 6,372,264 B1
(45) Date of Patent: Apr. 16, 2002

(54) METHOD OF REDUCING CALCIFIED ARTERIAL PLAQUE BUILDUP AND CELLULAR MALFUNCTION AND FOR BALANCING IONIC CALCIUM

(75) Inventor: Michael W. Dixon, Lake Forest, CA (US)

(73) Assignee: Gusty Winds Corporation, Costa Mesa, CA (US)

( * ) Notice: Subject to any disclaimer, the term of this patent is extended or adjusted under 35 U.S.C. 154(b) by 0 days.

(21) Appl. No.: 09/645,295

(22) Filed: Aug. 24, 2000

(51) Int. Cl.$^7$ .................. A01N 59/08; A61K 38/16; A61K 35/78; C07C 205/00
(52) U.S. Cl. .............. 424/677; 562/853; 424/681; 514/6; 530/370
(58) Field of Search ................. 424/677, 681; 514/6; 530/370; 562/853

(56) References Cited

U.S. PATENT DOCUMENTS 3,178,451 A * 4/1965 Reyes et al. .............. 260/343.7
5,849,337 A * 12/1998 Dixon ........................ 424/677

* cited by examiner

*Primary Examiner*—Alton Pryor
(74) *Attorney, Agent, or Firm*—Morland C. Fischer (57) ABSTRACT

A method for reducing calcified arterial plaque buildup and cellular malfunction with the administration of therapeutically effective dosages of a compounded coordination complex of magnesium. The method includes steps for making and administering a compounded coordination complex of calcium that balances ionic calcium and does not contribute to unbalanced calcium metabolism, cellular malfunction or calcified arterial plaque buildup. A standardized method for making a compounded coordination complex of inorganic minerals is also disclosed.

14 Claims, 3 Drawing Sheets

Tunica Intima
(inner layer):

Endothelium
    (Endothelial Cells)

Internal
    Elastic
    Lamina
    (Longitudinal
      Elastic Fibers and
      Connective Tissue)

Tunica Media
(middle layer)
    (Transverse Elastic
      and Muscle Fibers)

Tunica Adventitia
(outer layer):

External
    Elastic
    Lamina
    (Longitudinal
      Elastic Fibers and
      Connective Tissue)

Collagen and
    Elastic Fibers

FIG. 3

METHOD OF REDUCING CALCIFIED ARTERIAL PLAQUE BUILDUP AND CELLULAR MALFUNCTION AND FOR BALANCING IONIC CALCIUM

BACKGROUND OF THE INVENTION

1. Field of the Invention

The present invention relates to a method of reducing the buildup of the amount of calcified arterial plaque and reducing cellular malfunction with the administration of an adequate quantity of the biochemically and physiologically important mineral salt magnesium (Mg) and more particularly a more biologically active form of magnesium known as compound complex magnesium. In addition, the present invention relates to a method of balancing ionic calcium with the administration of an adequate quantity of the biochemically and physiologically important mineral salt calcium (Ca) and more particularly a more biologically active form of calcium known as compound complex calcium that does not contribute to calcified arterial plaque buildup and cellular malfunction.

2. Background Art

Magnesium salts are essential in human nutrition. As part of adenosine triphosphate (ATP), magnesium is required for all biosynthetic processes, glycolysis, formation of cyclic adenosine monophosphate (cyclic AMP), is involved in energy metabolism and energy dependent membrane transport, and is required for ribonucleic acid (RNA) synthesis and transmission of the genetic code. Magnesium salts (a cation) are required for the activity of more than 300 enzymes (either by interaction between substrate and an active site or by induction of conformational change), and especially those enzymes concerned with oxidative phosphorylation. Magnesium salts are an important component of both intracellular and extracellular fluids. Intracellular magnesium is believed to control cellular metabolism by modulating the activity of rate limiting enzymes. Extracellular magnesium is critical to the maintenance of electrical potentials of nerve and muscle membranes and for transmission of impulses across neuromuscular junctions. Magnesium salts are important in maintaining the homeostasis of cardiac and smooth muscle tissues. In each of these physiological processes there is an interaction with the mineral salt calcium, which may act synergistically or antagonistically.

It is believed that there are 20 to 28 grams of magnesium in the adult human body. Approximately 59% is in the body's skeleton and bone structures, approximately 40% is in the body's musculature and soft body tissues, with approximately 1% (about 2 to 2.8 grams) in the body's extracellular fluid. Serum concentration ranges from 1.1 to 2.1 mEq/l in healthy individuals and is believed to be regulated primarily by the kidneys. Kidney filterable magnesium (serum magnesium not bound to protein) is either reabsorbed in the kidneys' proximal convoluted tubule or in Henle's loop, which is where major adjustments in response to serum concentrations are believed to take place. There is a passive equilibrium between a portion of skeletal magnesium and that in the blood which is believed to act as a modulator against fluctuations in extracellular magnesium concentrations.

Magnesium balances calcium and its functions within the human body. It is believed that the adult human body contains approximately 1200 grams of calcium, with approximately 99% of it in the skeleton, and approximately 1% (about 12 grams) in extracellular fluids, intracellular structures, and cell membranes. This approximately 1% plays an essential role, in conjunction with magnesium, in the functions of nerve conduction, muscle contraction, blood clotting, and membrane permeability. It is believed that serum calcium concentration is maintained by several hormones, including estrogen and testosterone. It is known that dietary protein enhances calcium absorption, and dietary phosphorus causes calcium retention.

Magnesium deficiency is known to cause nausea, muscle weakness, neuromuscular and cardiac irritability, tetany, convulsions, tremors, mental depression, psychotic behavior, inhibit proper muscle function and contractions, as well as interfere with the proper utilization of calcium and potassium.

Magnesium is inorganic and is not produced by the human body. Humans must rely upon dietary sources to provide the body with its magnesium requirements. Magnesium is a natural component of the earth's crust and finds its way into the diet of humans from the food products grown in soil. Foods containing the highest concentration of magnesium are unprocessed whole grains, legumes, seeds, and chlorophyll containing green plant foods (the central atom of chlorophyll molecules is magnesium). More than 80% of the magnesium content of unmilled grains are lost by removal of the germ portion and by the removal of the outer layer (bran) of the grains during the milling process. Diets rich in refined and processed foods, meats, and dairy products are low in magnesium content, in addition to increasing calcium absorption caused by protein consumption, and calcium retention caused by phosphorus consumption (often in the form of phosphates from processed foods and sodas).

Dietary magnesium intake has declined in the United States, with a per capita decline of magnesium in the U.S. food supply (estimated as food flowing through the food distribution system) of from 408 mg/day in 1909 to 329 mg/day in 1986, almost a 20% decline. This is believed to be a relatively small decline when compared to many decades earlier when unrefined and unprocessed foods, along with a consumption of less meats and dairy products, were the dietary standard in the U.S. This closely correlates with the chemical analysis of typical U.S. diets in the Food and Drug Administration's Total Diet Study of 1976, 1977, 1980, 1981 and 1982, and with the United States Department of Agriculture's 1985 average magnesium intake of adult men, and the USDA's 1987 mean magnesium intake for adult women. The U.S. decline in dietary magnesium intake is directly attributable to the dietary decrease of unprocessed whole grains, legumes, seeds, and green plant foods, with a concurrent dietary increase of refined and processed foods, meats, sodas, and dairy products.

In those with normal digestion and assimilation, magnesium absorption from food is believed to be from approximately 40 to 60% of that ingested, with a slight reduction in absorption in the presence of phytate (a negatively charged form of phytic acid, i.e., inositol hexaphosphate found in plant leaves) or in the presence of fiber.

Magnesium depletion in humans can occur in those with inadequate dietary intake, excessive calcium intake (which disrupts calcium metabolism), excessive or prolonged levels of stress, gastrointestinal tract abnormalities associated with malabsorption, renal reabsorption dysfunction, excessive fluid and electrolyte losses of systemic or diuretic drug causes, and by the interference of certain drugs.

Large oral intakes of magnesium are generally regarded as safe, with no evidence of harm in those with normal renal function. It is known that excessive oral intakes of magnesium may cause transitory diarrhea.

Oral intakes of magnesium are naturally difficult for the body to absorb. It is believed that only 3 to 12% of elemental magnesium is absorbed for use by the body. Past attempts to increase the amount of magnesium made available for absorption by the body have been only partially successful until the development of compound complex magnesium.

While there is evidence that magnesium chelated with protein amino acids is more effectively absorbed by the body, passing more efficiently through the intestinal membrane into the blood than elemental magnesium, it is not completely clear how much more effective this is. Accordingly, there has been a degree of uncertainty attached to the selection of proper dosages of magnesium prior to the development of compound complex magnesium.

Compound complex magnesium is a compounded coordination complex of magnesium comprised of a coordination complex of magnesium, protein amino acids, and ascorbic acid in a ratio of 1:1:2, i.e., one part magnesium, one part protein amino acids, and two parts ascorbic acid, by weight. This composition of compound complex magnesium results in a balanced potential of hydrogen producing essentially a neutral pH factor (i.e., 0.0000001 gram atom of hydrogen ion per liter of solution essentially the same pH of distilled water). When prepared in the indicated manner, the anionic ascorbic acid component acts as a strong complexing agent capable of binding the cationic magnesium component, effectively producing a ligand coordination complex. In addition, the second complexing with the ascorbic acid component reinforces the first complexing of the magnesium component with the protein amino acids allowing it to reach its full potential, with an exponential increase in its potential for intestinal absorption, cell utilization and effectiveness. This double complexing process can be thought of as a stepped double complexing, or a compounded coordination complex, or a compound ligand, or simply a compound complex. This compounded coordination complex effectively potentiates the magnesium producing a composition which is essentially 100% available for intestinal absorption and cellular utilization resulting in maximum efficacy. Compound complex magnesium is an improvement over any other form of orally administered or ingested magnesium.

Compound complex magnesium has demonstrated greater intestinal absorption and cellular utilization, and when administered in effective amounts has the demonstrated ability to balance calcium metabolism, prevent dystrophic calcification, reduce and normalize blood pressure, relieve and control stress-induced cardiac arrhythmia extrasystole, prevent the formation of arterial plaque, prevent atherosclerosis, and to maintain the homeostasis of the cardiovascular system of the human body. This is more fully detailed in my prior U.S. Pat. No. 5,849,337 issued Dec. 15, 1998.

It is widely known that cardiovascular disease is the leading cause of death in the United States, as well as in most industrialized countries of the world. It is widely recognized that atherosclerosis is the main cause of cardiovascular disease. Atherosclerosis is characterized by calcified arterial plaque buildup, which results in reduced arterial blood flow and can eventually contribute to or manifest itself as heart attack, stroke, and peripheral arterial insufficiency. Calcified arterial plaque is arterial plaque that has been hardened by calcification with the mineral salt calcium. Recent advances in imaging equipment, most notably electron beam computed tomography, have made it possible to non-invasively and clearly view and measure calcified arterial plaque buildup in a functioning and beating heart without producing blurred images.

Recent research has revealed the main cause of calcified arterial plaque buildup to be unbalanced ionic calcium metabolism catalyzed by excessive free radicals in a collagen weakened arterial system of long duration. Ionic calcium is a form of calcium that is not bound to protein. It has been recently discovered that free unbound ionic calcium is the form of calcium that causes and contributes to cellular malfunction and unbalanced calcium metabolism, especially when ionic calcium is excessive and/or not balanced with a more bioavailable form of magnesium such as compound complex magnesium, and as a result causes and contributes to dystrophic calcification and the buildup of calcified arterial plaque at the sacrifice of other biologically important functions of calcium. Compound complex magnesium balances unbalanced calcium metabolism, preventing cellular malfunction and calcified arterial plaque buildup. There is a need for an improved form of calcium which can balance ionic calcium and not disrupt proper cellular function and not contribute to calcified arterial plaque buildup.

Past attempts at limiting arterial plaque buildup have generally been limited to controlling the "risk factors" such as dietary fat and cholesterol reduction, blood cholesterol lowering medications, and blood pressure lowering medications, all with less than 100% effectiveness and with sometimes substantial deleterious side effects. Past invasive treatments for arterial plaque buildup have included angioplasty, shunt implant surgery, and arterial graft bypass surgery. In addition to the risks inherent with these procedures, the redevelopment of arterial plaque buildup is well documented with it being known to generally reoccur at an accelerated rate at the site of the procedure.

Therefore, a need exists for a method of administration of compound complex magnesium which can effectively reduce calcified arterial plaque buildup and cellular malfunction in the human body, and a method for making an improved form of calcium which can balance ionic calcium and not disrupt normal cellular function or contribute to calcified arterial plaque buildup.

SUMMARY OF THE INVENTION

Briefly, and in general terms, a method is described for reducing existing calcified arterial plaque buildup and reducing cellular malfunction in the human body when a compound complex form of magnesium is administered orally. This is accomplished by administering effective amounts of compound complex magnesium which allows for greater intestinal absorption and cellular utilization, which has the ability to improve cellular function and increase cellular efficiency by reducing cellular malfunction, balance calcium metabolism, prevent dystrophic calcification and maintain the homeostasis of the cardiovascular system of the human body. In addition, a method is described for making an improved form of calcium which can balance ionic calcium and not disrupt cellular function, not contribute to cellular malfunction and not contribute to calcified arterial plaque buildup.

In accordance with these discoveries, it is an object of the invention to provide a method for selectively administering an improved magnesium composition, known as compound complex magnesium, when administered in an effective amount, which can reduce the formation or buildup of calcified arterial plaque.

It is another object of the invention to provide a method for selectively administering compound complex magnesium, when administered in an effective amount, which can reverse or lessen the progression of atherosclerosis. The term "atherosclerosis" is used herein to distinguish any form of cardiovascular disease, especially that which is characterized by arterial plaque formation or buildup, arterial constriction or spasm, thrombus formation, restricted or reduced arterial blood flow, or an increase in arterial blood pressure.

It is another object of the invention to provide a method for selectively administering compound complex magnesium, when administered in an effective amount, which can improve cellular function and increase cellular efficiency by reducing cellular malfunction.

It is another object of the invention to provide a method for making an improved form of calcium which can balance ionic calcium and not disrupt cellular function.

A further object of the invention is to provide an improved form of calcium which can balance ionic calcium which does not contribute to cellular malfunction.

A further object of the invention is to provide an improved form of calcium which can balance ionic calcium which does not contribute to dystrophic calcification.

A further object of the invention is to provide an improved form of calcium which can balance ionic calcium which does not contribute to calcified arterial plaque buildup.

A further object of the invention is to provide an improved form of calcium which can balance ionic calcium which is simple to produce and economically feasible to distribute on a commercial basis.

Other objects and advantages of this invention will become readily apparent from the ensuing detailed description and the clinical case studies.

DETAILED DESCRIPTION OF THE INVENTION

The term "compound complex magnesium" is used herein to identify the magnesium compound used in the present invention. Compound complex magnesium is a compounded coordination complex of magnesium comprised of a coordination complex of magnesium, protein amino acids, and ascorbic acid in a ratio of 1:1:2, i.e., one part magnesium, one part protein amino acids, and two parts ascorbic acid, by weight. This composition of compound complex magnesium results in a balanced potential of hydrogen producing essentially a neutral pH factor (i.e., 0.0000001 gram atom of hydrogen ion per liter of solution—essentially the same pH of distilled water). When prepared in the indicated manner , the anionic protein amino acids component acts as a strong complexing agent capable of binding the cationic magnesium component, effectively producing a ligand coordination complex. In addition, the second complexing with the ascorbic acid component reinforces the first complexing of the magnesium component with the protein amino acids allowing it to reach its full potential, with an exponential increase in its potential for intestinal absorption, cellular utilization and effectiveness. This double complexing process can be thought of as a stepped double complexing, or a compounded coordination complex, or a compound ligand, or simply a compound complex. This compounded coordination complex effectively potentiates the magnesium producing a composition which is essentially 100% available for intestinal absorption and cellular utilization resulting in maximum efficacy. Compound complex magnesium is an improvement over any other form of orally administered or ingested magnesium, and functions on the cellular level in conjunction with calcium.

It is believed there are at least ten mechanisms, or levels, at work that contribute to the effectiveness of compound complex magnesium: one is the double compounded complexing of magnesium; the second is the balancing of the potential of hydrogen of the compound; the third is the electrical anionic/cationic balance; the forth is the strong synergism of the components of the compound; the fifth is the ratio of the components of the compound; the sixth is the balancing of an inorganic dietary substance with an organic dietary substance; the seventh is the ability of the compound to balance calcium metabolism; the eighth is the compound's contribution to the homeostasis of the blood; the ninth is the compound's contribution to the homeostasis of the cardiac muscle and blood vessels; and the tenth is the compound's antioxidant benefit.

Because compound complex magnesium is substantially 100% available for absorption by the body's intestinal tract, administration may be more precisely controlled and limited to physiological amounts that satisfy the requirement. This provides an important advantage of compound complex magnesium in that it permits precise, preselected control over the amount of consumption to fit the need.

Because of the balancing properties of compound complex magnesium, it can be administered orally with foodstuffs or with other nutrients without interference of either, or can be administered on an empty stomach without gastric upset, and without any reduced effectiveness. Compound complex magnesium is well tolerated, even by those with certain types of systemic absorption difficulties, such as irritable bowel syndrome (IBS), in whom delayed or sustained release (also known as timed release) preparations can cause sometimes severe intestinal tract irritation.

Another major advantage of compound complex magnesium is the complimentary aspect of its ascorbic acid component. In addition to it balancing and assisting magnesium, some of its functions and benefits are very similar to those of magnesium, not the least of which is ascorbic acid's function with numerous enzymes, and its beneficial role in maintaining the homeostasis of cardiac and arterial smooth muscle tissues. Likewise, magnesium also compliments ascorbic acid by modulating the possible formation of oxalate crystals, i.e., calcium oxalate renal calculi. This synergism is a strong indicator of the likely mechanism of the compound's exponential efficacy. Like magnesium, ascorbic acid is generally regarded as safe, even with large intakes, in those with normal renal function. While it is known that excessive oral intakes of ascorbic acid may cause transitory diarrhea (essentially the same as excessive oral intakes of magnesium), when magnesium and ascorbic acid are joined together to form a compounded coordination complex of magnesium, there is an improved bowel tolerance seen. This occurs as a result of the improved intestinal absorption qualities of compound complex magnesium, allowing for ingestion of larger effective dosages of compound complex magnesium than would otherwise be possible with either magnesium or ascorbic acid ingested individually or ingested together but not joined together to form a compounded coordination complex.

In accordance with the present invention, and as will be demonstrated below, an unexpected discovery and benefit from the administration of compound complex magnesium is to provide a protective advantage for the cardiovascular system by reducing calcified arterial plaque buildup and thus lessening the progression of atherosclerosis. A further unexpected discovery and benefit from the administration of compound complex magnesium is to improve cellular function and increase cellular efficiency by reducing cellular malfunction. Compound complex magnesium provides a distinct improvement over any other form of orally administered cardiovascular disease prevention composition and is the only composition which has the demonstrated ability to balance calcium metabolism, prevent dystrophic calcification, reduce the amount of calcified arterial plaque buildup, reverse the progression of atherosclerosis and reduce cellular malfunction, without any deleterious side effects. Its effectiveness and safety in the living human body have been shown, as will be detailed in the clinical case studies below.

The following clinical case studies are only to further illustrate the present invention and are not intended to limit the true spirit or scope of the invention.

Clinical Case Studies

All clinical studies were conducted on living human beings, not lab animals or cadaver tissues. The clinical studies presented herein are typical as to the methodology, test subjects and results. All results of the clinical studies have been independently verified on a double-blind basis.

A 58 year old male subject was presented with clinically diagnosed atherosclerosis, specifically with calcified arterial plaque buildup present in the left coronary artery located just before the artery's bifurcation, with a somewhat lesser amount of calcified arterial plaque buildup in the aortic arch. This was independently verified by electron beam computed tomography scan (EBCT scan) along with other standard diagnostic tests also independently conducted and verified. The calcified arterial plaque buildup as seen in the subject is typical of the location and progression as seen in clinically diagnosed atherosclerosis patients. The amount of calcified arterial plaque was carefully measured to determine the level of risk for a coronary event, as well as to track the rate of the plaque's progression or regression. An independent risk assessment established the subject's level of risk for a coronary event as "moderate."

All clinical lab work was conducted on an independent double-blind verification basis where each lab's work was verified by a second independent lab without the knowledge of the other lab's involvement, and with none of the doctors, nurses, technicians or directors at any of the labs knowing of the compound complex magnesium regimen the subject was placed on after calcified arterial plaque buildup was discovered in the subject. The same EBCT scanning facility and the same calibrated EBCT scan machine were used for all follow-up arterial scans to maintain consistency, but none of the EBCT scanning facility staff and personnel knew of the compound complex magnesium regimen of the subject. The subject's age, weight, body fat distribution (with excess around the middle), blood pressure (moderately elevated), blood cholesterol (elevated, with total blood cholesterol 251–264 mg/dl), family history, stress level, and calcified arterial plaque distribution and location were all more or less consistent with that typically seen in male subjects of the same age and state of health. The subject used was a typical test subject.

Figure 1:
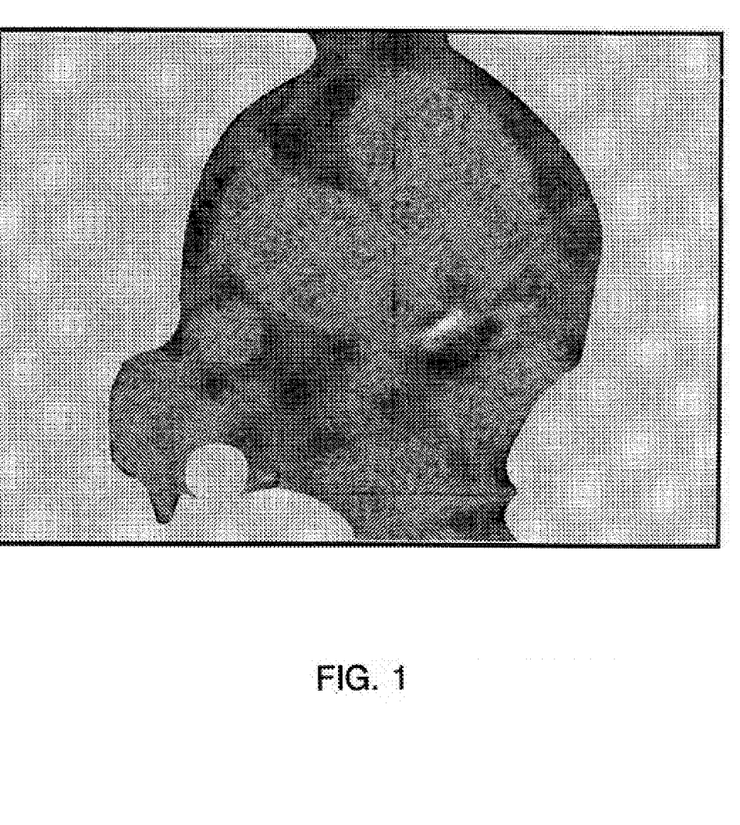
FIG. 1 illustrates by electron beam CT scan the calcified arterial plaque buildup in the left coronary artery of a human subject prior to the administration of the magnesium compound regimen according to the method of the present invention.

The EBCT scan that shows the calcified arterial plaque buildup in the subject's left coronary artery prior to the administration of the magnesium compound regimen according to the method of the present invention is depicted in FIG. 1.

The subject was placed on an exact regimen of compound complex magnesium administration ranging from 2000 to 3000 mg/day in divided dosages (usually 1000 mg taken after each meal), while maintaining a normal diet consisting of approximately 15–25% protein, 25–35% fats, and 40–60% carbohydrates. It was observed that the subject appeared to benefit the most at the 3000 mg/day level of compound complex magnesium administration, with this level being twice the amount previously thought to be the maximum (and twice the prevention level), with no deleterious side effects of any kind. This reinforces the knowledge that compound complex magnesium is exceedingly safe to administer, even in dosages up to and including 3000 mg/day for long periods, in subjects with normal renal function. The subject's renal function was regularly monitored, with his serum creatinine consistently within the normal reference range of 0.7–1.3 mg/dl. The subject was not on any medications or other unusual substances, was a non-smoker, moderately active, and nothing else was unusual or remarkable in lifestyle except for the compound complex magnesium regimen. The subject was carefully monitored with regular independent full blood tests, complete workups, doppler ultrasounds, and EBCT scans of the arterial system.

Six months after the EBCT scan revealed the presence of calcified arterial plaque buildup in the subject's left coronary artery and the aortic arch, and six months after the subject began the compound complex magnesium regimen, a follow-up EBCT scan conducted at the same independent lab facility on the same calibrated EBCT scan equipment revealed a 27.3% annual decrease in the amount of calcified arterial plaque in the subject's left coronary artery with a similar degree of calcified arterial plaque reduction seen in the subject's aortic arch. Arterial plaque progression (or reduction) is expressed as the rate of annual increase (or decrease) because it had been generally believed that the formation of calcified arterial plaque only increased rather than decreased, with such increase occurring relatively slowly over a period of years. However, by virtue of my discovery described in the present invention, it has now been demonstrated and independently verified that calcified arterial plaque buildup can be reduced, and reduced relatively easily and quickly, and with no deleterious side effects.

Figure 2:
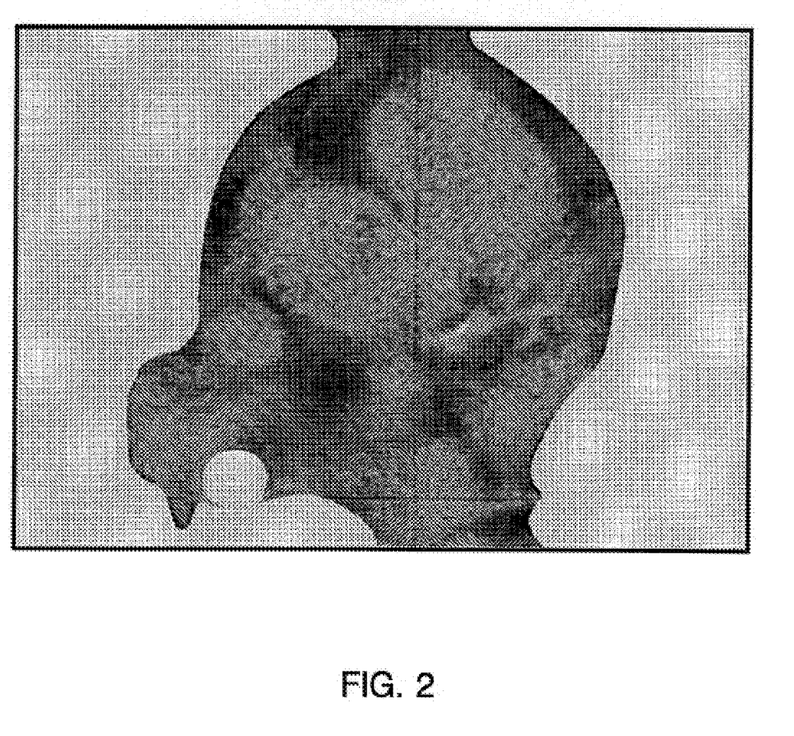
FIG. 2 illustrates by electron beam CT scan a reduction of the calcified arterial plaque buildup at the same location in the left coronary artery of the same human subject of FIG. 1 following the administration of the magnesium compound regimen according to the method of the present invention.

The EBCT scan that shows a reduction of the calcified arterial plaque buildup in the subject's left coronary artery following the administration of the magnesium regimen according to the method of the present invention is depicted in FIG. 2.

It is well-known that calcified arterial plaque buildup does not spontaneously reverse. A carefully detailed examination of the subject revealed that nothing else in lifestyle was unusual or could otherwise account for the reduction of the calcified arterial plaque observed. The method of administration of the magnesium compound according to the present invention has demonstrated a profound beneficial effect upon the cardiovascular system specifically reducing calcified arterial plaque buildup, thus reversing and lessening the progression of atherosclerosis.

Arterial plaque is a complex mixture of fibrin, cholesterol, lipids, platelets, cell debris and calcium. It is associated with weakened and damaged arteries, the body's blood clotting mechanism, cellular malfunction and with calcification.

EBCT scan is current state-of-the-art non-invasive imaging equipment that allows for clear visual images and exacting calcified arterial plaque measurements. Because of the increased speed of exposure, EBCT scan has the ability to produce images of the functioning, beating human heart without producing blurred images and with limited radiation exposure. In 1997, the American Heart Association (AHA) recognized the use of EBCT scan for atherosclerosis diagnosis: "Electron-beam CT can also be used to measure calcium deposits in the coronary arteries. The amount of calcium detected by EBCT is related to the amount of underlying coronary atherosclerosis." In 1996, the AHA stated: "A total of 2,745 asymptomatic patients . . . show the coronary calcium score is highly predictive of future cardiac events. The [EBCT] scanning technique [is] more than 10 times more powerful a predictor of coronary disease episodes than [blood] cholesterol testing."

Accordingly, I have discovered that compound complex magnesium when administered in an effective amount has a profoundly beneficial influence on the homeostasis of the body's cardiovascular system, and that compound complex magnesium has the ability to reduce calcified arterial plaque buildup as verified by the use of EBCT scans.

Compound complex magnesium's ability to reduce calcified arterial plaque buildup is centered around proper cellular metabolism and functioning in conjunction with calcium.

It is well-known that magnesium is critical for cellular function. It is thought that the proper balance of magnesium and calcium contribute to proper cellular function. Excessive calcium, or excessive ionic calcium, especially in the face of inadequate magnesium, disrupts proper cellular function. Excessive unbalanced ionic calcium enters cells and accumulates causing reduced cellular efficiency and malfunction. Although cellular malfunction occurs throughout the entire cell in the presence of excessive unbalanced ionic calcium, it is believed that the biologically active mitochondria and endoplasmic reticulum are the organelles primarily affected. The mitochondria produces energy in the form of adenosine triphosphate, known as ATP synthesis, allowing vital cellular chemical reactions to occur throughout the human body. This occurs during the normal cellular metabolism process, which liberates free electrons and transports them through a series of proteins known as the electron transport chain. The result of this movement of electrons develops an electrical potential across the inner mitochondria membrane, and the energy developed is used as the driving force for ATP synthesis. Critical to ATP synthesis and proper cellular metabolism is adequately absorbed and properly utilized magnesium. Insufficient magnesium, and/or insufficiently absorbed magnesium, and/or excessive calcium, and/or excessive ionic calcium, especially of long duration, disrupts normal ATP synthesis of the mitochondria causing malfunction. Mitochondria dysfunction severely affects overall cellular metabolism, energy production, and eventual cellular survival. It is now believed that cellular mitochondria malfunction and decay may be the primary factor in the aging process and degenerative diseases. It is believed that contributing to these processes are excessive free radicals. Free radicals are a byproduct of cellular oxygen utilization which can accumulate and damage the entire cell as well as the mitochondria without adequate levels of balancing antioxidants. Closely associated with this is the functioning of the endoplasmic reticulum which stores calcium, releases it for use, then stores it after use. The endoplasmic reticulum is that portion of the cell where many of the cell's chemical activities take place. Unbalanced ionic calcium metabolism, excess calcium, and/or excess ionic calcium can disrupt the normal functioning of the endoplasmic reticulum and contribute to cellular malfunction. Compound complex magnesium when administered in effective dosages and by balancing calcium metabolism can effectively improve cellular function and increase cellular efficiency by reducing cellular malfunction, contributing to cellular homeostasis.

The mechanisms responsible for the beneficial effects observed as a result of administering the compound complex magnesium composition are the interaction of the composition with calcium on several different but closely related levels, especially the ability of compound complex magnesium to balance calcium metabolism, prevent dystrophic calcification, the arterial strengthening and elasticity support provided by the composition, the free radical damage prevention qualities of the composition, and the unusually complimentary synergism of the compound's components with its exponential increase of effects in vivo.

Impairment of calcium metabolism, thought to be catalyzed by free radical damage, allows excessive ionic calcium to enter cells resulting in damage and malfunction. It is known that calcium activates phospholipase-A, which cleaves arachidonic acid from membrane phospholipids. Arachidonic acid produces prostaglandins and leukotrienes, which create free radicals. The inflammatory substances leukotrienes attract and stimulate leukocytes, which produce superoxide free radicals during phagocytosis causing free radical damage to surrounding tissues. Damaged blood vessel arterioles and capillaries dilate causing edema and erythrocyte leakage through the blood vessel walls. Microthrombi is produced by stimulated platelets, while erythrocytes release free iron and copper which causes an increase of tissue damage. Excessive ionic calcium in smooth muscle cells (i.e., blood vessel cells), as a result of free radical damage to the cells, is bound to calmodulin activating myosin kinase, which phosphorylates myosin causing myosin and actin to constrict producing muscle cell contraction. The same thing occurs in cardiac muscle cells. Increased ionic calcium within muscle cells can cause muscle spasm. When constriction occurs in the smooth muscle fibers of the blood vessels, blood flow is reduced and blood pressure is increased. When constriction occurs in the cardiac muscle fibers of the heart, angina or even myocardial infarction can occur. It is known that excessive intracellular calcium impairs myocardial function by reducing oxygen utilization efficiency. Intracellular calcium excess also results from increased ionized serum calcium levels which slowly increase with age, partially as a result of excessive dietary phosphates, making it more difficult to prevent excessive calcium from entering cells. Stress, another factor, causes retention of cellular calcium as a result of stress increased circulating catecholamines, which lessens the integrity of magnesium calcium ATPase. When metabolized, catecholamines produce free radicals. Free radicals have been implicated in atherosclerosis.

Magnesium is a natural calcium channel blocker that inhibits the entry of calcium into cells and inhibits the mobilization of calcium from intracellular stores, resulting in slowing of atrioventricular and sinoatrial conduction and relaxation of arterial smooth and cardiac muscle. This accounts for the blood pressure lowering and normalizing effect seen in the subject. Magnesium counters the effects of calcium induced stress. It is believed that a complex sequence of events involving calcium metabolism which results in free radical damage, along with stress, are the basis for atherosclerosis. The improper utilization of calcium appears to be at least part of the atherosclerosis equation. Compound complex magnesium helps stabilize and balance calcium metabolism, thus normalizing its functions.

It is well-known that one of the components of calcified arterial plaque is calcium. It was originally thought that calcification of arterial plaque occurred in the later stages of plaque formation, however it is now known that serum calcium (specifically ionic calcium) is present throughout the arterial plaque formation and buildup process. Regular high serum levels of magnesium, as provided by compound complex magnesium, are believed to help prevent and contribute to reduction of plaque calcification by balancing and normalizing serum calcium's functions. Although magnesium has a known antagonistic quality with calcium, it does not use up or eliminate calcium but rather balances its functions. This was evidenced by the subject's monitored serum calcium levels during the compound complex magnesium regimen, which consistently remained within normal ranges from 8.8 to 9.9 mg/dl, without any calcium being administered. It is believed that administered excessive calcium, or ionic calcium, may exacerbate unbalanced calcium and its detrimental effects.

In a 1999 study conducted at University of California Los Angeles it was found that 90% of 39 kidney dialysis patients, who required "super-high" doses of calcium as part of their treatment regimen, developed "serious coronary-artery calcification" as detected by EBCT scan, and this occurred even in those as young as in their 20's which is at least 20 years earlier than typically seen. In a related study released April 1998 by the AHA conducted by the Edinburgh Artery Study, funded by the British Heart Association, involving 1,106 participants which compared blood vessel thickness with blood flow status and levels of various blood substances, it was found that "sticky" blood marked the early development of atherosclerosis in men: "The study noted significant correlations in men—but not women—between intima-media thickness [the inner and middle layers within the artery wall believed to be where arterial plaque deposits form] and elevated blood viscosity and three major elements that determine blood stickiness: plasma viscosity, fibrinogen, and red-blood-cell count." Fibrinogen is a blood protein which can be transformed by thrombin into a fibrin clot, with levels elevated above 277 mg/dl being thought to contribute to atherosclerosis risk, and is now one of the blood components that is measured by state-of-the-art labs. This finding correlates with calcium's role as a blood coagulation factor, as well as a blood clotting factor. It is well-known that calcium is a required factor in several phases of blood coagulation (blood coagulation Factor IV), especially with fibrinogen (blood coagulation Factor I), and contributes to blood viscosity and stickiness.

Homocysteine, a metabolic byproduct of the amino acid methionine thought to be mitigated by adequate administration of the vitamins pyridoxine (B-6), cyanocobalamin (B-12), and folic acid (folate), elevated levels of which are found in 20–30% of patients with atherosclerosis, was monitored in the subject and was consistently found to be within the normal reference range of 4–14 nmol/ml with an average of 8.1 nmol/ml.

It is well-known that ascorbic acid maintains the homeostasis of the body's collagenous structures, such as the blood vessels. A clinical deficiency in ascorbic acid leads to the serious condition of scurvy, which is characterized by the weakening of the blood vessels resulting in widespread capillary hemorrhaging. It is believed that a subclinical deficiency in ascorbic acid, especially of long duration, still weakens the blood vessels but less severely than a clinical deficiency. Because of the generally weakened nature of the blood vessels, a subclinical deficiency may manifest itself as bleeding gums or as very small blood vessel hemorrhages. As the body repairs the very small hemorrhages the natural repair materials and functions, such as the formation of intrinsic and extrinsic prothrombin and thrombin and then the formation of stable fibrin polymers, contribute to atherosclerosis. It is believed that regularly administered compound complex magnesium prevents these conditions because of the effects of its ascorbic acid component and because of the compound's unusually strong magnesium synergy resulting in making the ascorbic acid component even more effective. It is also believed that because of the nature of the ascorbic acid component being a strong antioxidant it further contributes to the reduction of calcified arterial plaque buildup as a result of its ability to protect the body from free radical damage, which is thought by many to be the root cause of atherosclerosis. Generally, administered compound complex magnesium can be thought of as producing a normalizing effect on the blood, the heart, and on the blood vessels, which are obvious complimentary functions.

Compound complex magnesium and calcium function on the cellular level on an interrelated basis. It is believed that ionic calcium disrupts the cellular metabolism of the artery endothelial cells at the site of collagen weakened, irritated (well-known to occur in carotid arteries of smokers), and/or blood turbulence locations (typically seen at artery bends such as the aortic arch, and at or near artery bifurcations), catalyzed by excessive free radical production and damage, with the components of arterial plaque beginning to form at the site. As the arterial plaque increases in size it protrudes into the artery lamina completely involving the thickness of the tunica intima and spreading to involve the tunica media. The plaque also protrudes into the artery interior, giving rise to it obstructing blood flow, calcification, possible arterial spasm and/or constriction, possible plaque rupture, and possible thrombus formation. While excessive ionic calcium is a causative factor, compound complex magnesium balances unbalanced calcium metabolism and has been proven to reverse the process as evidenced by its ability to reduce calcified arterial plaque buildup.

Figure 3:
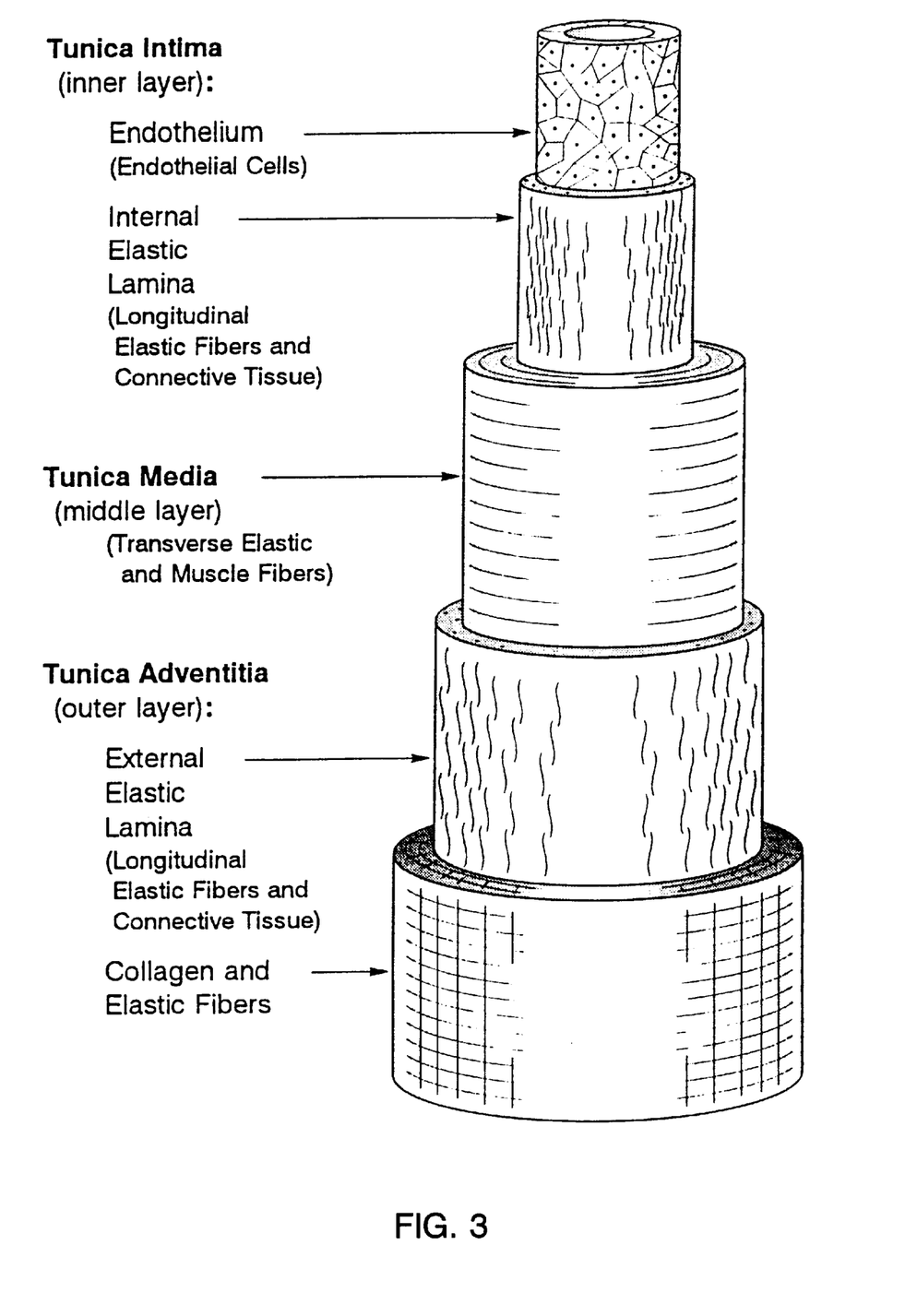
FIG. 3 illustrates the basic artery structure of a human being to facilitate a clearer understanding of the mechanism of effect of calcified arterial plaque buildup and for explaining the effects and advantages of the magnesium compound according to the method of the present invention.

To help facilitate a clearer understanding as to how these complex processes come together to effect the arteries of human beings, the basic artery structure is depicted in FIG. 3.

It has been generally thought that consumption of large amounts of the mineral calcium are necessary to maintain good health in adulthood, primarily to prevent osteoporosis. Recent research of calcium and a close examination of its biological role in the function of the human body reveals some quite significant incongruities between the commonly held perceptions and the realities, and adds perspective to the true value of dietary calcium, as well as its shortcomings.

Calcium, like all minerals, originates in the earth. Thus calcium is a natural constituent of soil and water and enters the diet with the consumption of plants grown in soil, from the water consumed, and in the U.S. for about the last 100 years or so from the high consumption of dairy products (cows consume the plants, which concentrates the calcium in their milk), which the U.S. government states contributes 55–60% of the calcium intake of the U.S. population. In addition, calcium most recently has been added to all manner of manufactured foods as "fortification" or "enrichment" and is the main ingredient in the most popular antacid preparations (currently the single largest volume of medication consumed in the U.S.).

Calcium has several important functions in the human body. Calcium helps form skeletal bones throughout the formative years (childhood up to about the age of 25) during which longitudinal bone growth occurs. After the longitudinal bone growth stops, their thickness and density continues to grow until about age 35 when peak bone mass is believed to be established. In spite of the fact that calcium is a major constituent of bone it is only one of several factors essential for its proper utilization and bone formation. Heredity influences bone mass, while hormones and physical activity influences bone metabolism. Other essential nutrients required for proper calcium utilization and bone formation include magnesium, copper, zinc, manganese, fluorine, silicon, boron, silica, strontium, folic acid, vitamin B-6, vitamin C, and vitamin D, as well as adequate protein amino acids to form collagen (bones are formed from collagen that have been hardened with calcium and the other minerals, with this known as mineralization). As peak bone mass is attained the greatest amount of bone mineralization is required for new bone growth, and the greater the peak bone mass the greater the retained bone density and bone strength as aging occurs. Bone loss gradually occurs with age, and for women it is accelerated at the time of menopause as a result of reduced estrogen production, with bone loss in men generally lagging about 10 or 15 years behind that of women. Dietary calcium and supplemental calcium intake have very little effect on bone loss in mature adults, while estrogen replacement therapy in postmenopausal women has been shown to reduce the rate of bone loss. It is believed that isoflavones from soy also help slow bone loss in mature adults.

Most stored calcium resides in the bones. Like the muscles, the bones deteriorate (a process known as atrophy) with lack of regular physical activity, and is the basis for osteoporosis as aging occurs. It is known that those who stay active and physically fit as they age are generally stronger and more robust longer, and retain stronger bones (and as a result do not overload the body with excess calcium released from the bones which typically is seen in those less active as aging occurs).

It has been demonstrated that older people can build muscle and strength with the right type of weight training exercises, and can even build bone if the right kind of exercises are continued for a long enough period of time (soft tissues like muscles respond quicker than harder tissues like the connective tissues tendons and ligaments, and eventually the bones; the harder and denser the tissue, the slower the adaptive response). This is a result of the human body's adaptive mechanism when a measured amount of stress (weight training) is regularly applied over time, and is currently considered the best osteoporosis prevention.

Factors that draw calcium from the bones are caffeine, processed foods, excess animal protein, sodas, refined carbohydrates, sugar, excess sodium, stress, and lack of regular physical exercise. Calcium that is drawn from the bones is released into the bloodstream as ionic calcium, thus being a contributor to unbalanced calcium metabolism, dystrophic calcification and calcified arterial plaque buildup. It is now believed that those factors that contribute to osteoporosis, are some of the same factors that contribute to atherosclerosis.

Ninety-nine percent of calcium in the human body is stored in the bones. The remaining 1% of calcium is critical in such vital functions as nerve conduction, muscle contractions, blood coagulation, blood clotting and membrane permeability. In the face of inadequate calcium intake or absorption the calcium stored in bones is sacrificed to maintain adequate calcium levels for vital functions. Calcium concentrations in the blood and soft tissues are believed to be maintained by interactions with several hormones and other nutrients, most notably magnesium and phosphorus.

Excess calcium intake, especially excess ionic calcium intake, and/or without sufficient amounts of the balancing nutrients (primarily magnesium, especially compound complex magnesium), unbalances and disrupts the body process by which calcium is assimilated and properly utilized (calcium metabolism). Chronically unbalanced calcium metabolism can cause calcium to be deposited and stored unnaturally in soft tissues. Unbalanced calcium metabolism is what causes dystrophic calcification, and is the basis for calcified arterial plaque buildup. This is a recent and quite important discovery.

It had been thought that excessive amounts of calcium only overburdened the excretory efforts of the liver and kidneys, induced constipation, and increased the risk of urinary stone formation (kidney stones). With the recent discovery of excessive amounts of unbalanced ionic calcium being the cause of dystrophic calcification of soft tissues, the negative side of calcium is now beginning to be better understood. It is believed that it is the ionic calcium component of calcium that is primarily responsible for dystrophic calcification, rather than the protein-bound calcium component (an excess of which is believed to be adequately handled by the liver and kidneys as long as the excess is not too great). This is supported by strongly mounting evidence in several clinical studies and epidemiological studies. Ionic calcium is distinguished by it containing a positive charge of electricity, hence it being a cation electrolyte, which when unbalanced may give rise to its ability to attract and fuse to soft tissues (such as in arterial plaque formation). It has also been discovered that dystrophic (or metastatic) calcium is deposited at tumor formation sites, as verified by EBCT scan, suggesting a possible link to tumor formation.

Calcium is not used in the sense that it is degraded during its biological functions and then needs to be continually replenished. Rather it is withdrawn from storage, used, and then returned to storage with very little loss. Calcium's use is typified in muscle contractions where it is stored in the endoplasmic reticulum portion of cells, from which it is released when muscle contractions are activated, then it is returned for storage after use.

It is now known that the amount of calcium needed by the human body for its biological functions is less than commonly believed, and is much less than many people in the U.S. are believed to consume. In a landmark study of calcium consumption and arterial disease, entitled: "Is calcium excess in Western diet a major cause of arterial disease?" published in the International Journal of Cardiology, 1991, 33:191–198, by British researcher Dr. Stephen Seely of the Department of Cardiology, University of Manchester, The Royal Infirmary, Manchester, U.K., the daily requirements of the human body for calcium are carefully delineated. The study correlates excess calcium consumption as a major contributory factor of unbalanced calcium metabolism, dystrophic calcification and the formation and buildup of calcified arterial plaque. The study also presents a strong case for a recommended dietary intake of calcium that is below the current Recommended Dietary Allowance (RDA), indicating compelling evidence of negative health consequences of excessive and/or unbalanced calcium ingestion. Included in the study are several supporting epidemiological studies referenced where it has been found that in countries where the calcium intake is within 200–400 mg/day arterial diseases are non-existent, and blood pressure does not increase with age. By contrast, in countries where the calcium intake is around the RDA (800–1200 mg/day) arterial diseases are common, while in countries where the calcium intake is well in excess of the RDA arterial diseases are rampant. The study presents considerable convincing evidence that, except for pregnant women who should get 650 mg/day in their last trimester of pregnancy (and during lactation), a dietary intake of calcium of between 300–400 mg/day for young adults and between 200–300 mg/day for older adults is sufficient to completely satisfy all bodily requirements of most people under normal conditions. These recommendations represent significant differences from the amount of dietary calcium intakes commonly ingested in the U.S., and other countries that consume the typical Western diet, where studies show that typical daily dietary calcium intake totals can reach more than 10 times the study's recommendations (2000–4000 mg/day).

Given the amount of dairy products, calcium enriched foods, calcium supplements and antacids consumed in the U.S., it is easy to see that contrary to current popular dogma the typical American diet contains many times more than the optimum amount of dietary calcium. Dietitians and many doctors apparently consider such levels of calcium consumption normal and desirable without fully understanding or appreciating the consequences of excessive calcium consumption and its connection to unbalanced calcium metabolism, dystrophic calcification and cardiovascular disease.

The RDA for daily calcium intake, set by the Food and Nutrition Board, Commission on Life Sciences, of the National Research Council (indicated on manufactured food package labels as "Percent Daily Value") are approximately 3–4 times the optimum amounts revealed in the study. However, the Food and Nutrition Board of the National Research Council does recognize and acknowledge in their standard book of RDA that: "many population groups seemingly maintain satisfactory [health] status with much lower intakes of calcium than the RDA." Another important aspect of calcium intake often overlooked is that the RDA is for "a total calcium intake" from all sources combined (that which is normally ingested in the diet, calcium supplements, and antacids and medications combined each day). It is now known that excessive amounts of total calcium intake, and/or excessive amounts of ionic calcium intake, contribute to unbalanced calcium metabolism, dystrophic calcification, cellular malfunction and calcified arterial plaque buildup in the human body.

It is known that excessive amounts of unbalanced or ionic calcium is also responsible for elevating blood pressure, a recognized part of cardiovascular disease. A typical area prone to arterial calcification is the aorta. The aorta functions by virtue of its elasticity to help provide the blood supply throughout the body during systole, and to the heart during diastole. The heart is unique among the body's organs in its dependence upon the diastolic pressure to provide its blood supply. The diastolic pressure that feeds the heart muscle is dependent upon the elasticity of the aorta, and is driven by the temporarily stored expansion energy provided by the systolic pressure as it expands the aorta. If diastolic pressure is reduced (because of lessened aortic elasticity), the body compensates by elevating the systolic pressure to maintain the diastolic pressure (obviously critical to feed the heart). One of the key factors in maintaining healthy aortic elasticity, in addition to maintaining healthy elasticity of all the blood vessels, is healthy collagen supported by adequate amounts of vitamin C. Lessened aortic elasticity necessitates a higher systolic pressure in an attempt to expand the aorta to its previous normal volume so that the diastolic pressure is not allowed to drop. Calcified arterial plaque buildup in portions of the aorta (typically seen in the aortic arch) reduces its functional elasticity and as a result elevates blood pressure. If calcified arterial plaque buildup is concurrently present in the coronary arteries narrowing them, thus further increasing blood flow resistance, a further rise in blood pressure will occur. As blood pressure increases, so does the workload of the heart. As the workload of the heart increases, so does its need for oxygen and nutrients. Thus, as calcified arterial plaque takes hold and gradually continues to increase in the aorta and other arteries, there is a gradual spiralling cycle of increasing blood pressure at the expense of the functional reserve and overload capacity of the heart (eventually weakening the heart, which may be a precursor to congestive heart failure often seen in the elderly with a history of chronic hypertension). This is believed to be one of the basic causes of high blood pressure as aging occurs, and is why hypertension is considered part of cardiovascular disease.

Dairy products, foods fortified with calcium, calcium supplements, and antacids are the primary sources of excess total calcium and ionic calcium in the diet. The nutrient content of cow's milk is significantly different than human breast milk (cow's milk has 1250 mg of calcium per liter—as compared to human breast milk which has about 330 mg of calcium per liter). Cow's milk has high phosphate levels and is acidic, both of which can contribute to unbalanced calcium metabolism. There is an excessive amount of calcium and saturated fat in cow's milk. There is 10 times more calcium in cow's milk than there is magnesium. It is known that excess intracellular calcium interferes with several aspects of proper cellular function, such as the proper use of insulin's ability to deliver glucose into the cells (another way in which diabetes and atherosclerosis may be connected). The acidic nature of cow's milk (because of its animal protein content) if consumed in excess tends to draw balancing alkaline calcium from the bones, and in so doing weakens the bones.

Studies have shown that cheese is the only known dairy product that doesn't seem to contribute to unbalanced calcium metabolism, dystrophic calcification and calcified arterial plaque buildup in spite of its saturated animal fat content. A study of the cheese making process reveals why. During the cheese making process the whey portion, the thin watery part of milk that separates from the thicker part (curds) after coagulation, is routinely discarded. The calcium content of the discarded whey is predominately ionic calcium, supporting the discovery that it is excessive ionic calcium (in the absence of adequate balancing magnesium) that is the primary cause of unbalanced calcium metabolism that contributes to dystrophic calcification and calcified arterial plaque buildup. It was believed that the type of cheese may also have been a factor, with the softer cheeses contributing less to arterial plaque by virtue of them containing less saturated animal fat. It is now believed that in spite of the saturated animal fat content of cheese, the primary reason cheese does not seem to contribute to unbalanced calcium metabolism, dystrophic calcification and calcified arterial plaque buildup is because of its lessened ionic calcium content. The ionic calcium content of cheese appears to be a stronger influence in calcified arterial plaque buildup than the well-known saturated animal fat content, with this being supported by several epidemiological studies.

It is believed that heredity contributes no more than 6–10% of the predisposition to cardiovascular disease. It is widely believed that about 40–44% of cardiovascular disease is caused by the "risk factors" of improper diet, elevated blood cholesterol, lack of regular physical exercise, smoking, stress, diabetes, obesity, and hypertension. But the remaining approximately 50% of the cause of cardiovascular disease has remained elusive to conventional medical research until now. Unbalanced calcium metabolism (caused by excess ionic calcium in the face of insufficient availability of the balancing nutrients, such as compound complex magnesium and an improved compound complex form of calcium) can be thought of as that missing link. More than just a factor the way excess dietary animal fats, hydrogenated trans fats, and elevated triglycerides (elevated by excess dietary refined carbohydrates and sugar) are, unbalanced ionic calcium metabolism is now believed to be the primary cause of calcified arterial plaque buildup and atherosclerosis. Compound complex magnesium has been proven to reduce calcified arterial plaque buildup, while it is believed that an improved complex of calcium tends to balance ionic calcium while providing the body with a form of calcium it needs for normal calcium functions and cellular metabolism.

With the discovery that unbalanced ionic calcium metabolism is the main cause of calcified arterial plaque buildup, and having established a need for a form of calcium which is not ionic and can balance ionic calcium, a method for making an improved form of calcium has been discovered and is now disclosed.

More particularly, a method has been discovered for making an improved complex of calcium which is a compounded coordination complex of calcium. The term "compound complex calcium" is used herein to identify the calcium compound of the present invention. Compound complex calcium is a compounded coordination complex of calcium comprised of a coordination complex of calcium, protein amino acids, and ascorbic acid in a ratio of 1:1:2, i.e., one part calcium, one part protein amino acids, and two parts ascorbic acid, by weight. This composition of compound complex calcium results in a balanced potential of hydrogen producing essentially a neutral pH factor (i.e., 0.0000001 gram atom of hydrogen ion per liter of solution essentially the same pH of distilled water). When prepared in the indicated manner, the anionic protein amino acids component acts as a strong complexing agent capable of binding the cationic calcium component, effectively producing a ligand coordination complex. In addition, the second complexing with the ascorbic acid component reinforces the first complexing of the calcium component with the protein amino acids allowing it to reach its full potential, with an exponential increase in its potential for intestinal absorption, cellular utilization and effectiveness. This double complexing process can be thought of as a stepped double complexing, or a compounded coordination complex, or a compound ligand, or simply a compound complex. This compounded coordination complex effectively potentiates the calcium producing a composition which is essentially 100% available for intestinal absorption and cellular utilization resulting in maximum efficacy. Compound complex calcium is an improvement over any other form of orally administered or ingested calcium, and because it is not free unbound ionic calcium it does not contribute to unbalanced calcium metabolism, dystrophic calcification or calcified arterial plaque buildup.

Compound complex calcium is prepared by one of two methods: by adding two parts ascorbic acid to an aqueous solution of one part water soluble salt of calcium complexed with one part protein amino acids, then recovered and dried by any conventional procedure; or simply, under ambient conditions, by completely blending two parts ascorbic acid with one part calcium complexed with one part protein amino acids. The resulting compounded coordination complex calcium composition is not ionic and is fully potentiated.

The following examples are only to further illustrate the present invention and are not intended to limit the true spirit or scope of the invention.

EXAMPLE 1

In a nonreactive glass vessel, 500 mg. calcium carbonate (USP) complexed in equal proportion with amino acids from vegetable protein was dissolved in 100 ml. distilled water at room temperature. Thereafter, 1000 mg. ascorbic acid (USP), of vegetable source, was added to the solution and the solution was stirred continuously. The glass vessel containing the solution was placed into a heating vessel. Then water was added to the heating vessel to just above the height of the solution, with the solution within the glass vessel and the water in the heating vessel never coming into contact. The heating vessel water was then heated to a boil, while the solution within the glass vessel was stirred continuously. Without bringing the solution to boil, the solution was heated and stirred until the mixture of the solution had completely dissolved, after which the glass vessel was submerged in an ice bath and then stored in a refrigerated compartment for 24 hours. After 24 hours the crystals were separated and freeze dried. Assay of the crystals showed that the coordination complex conversion of compound complex calcium contained approximately 425 mg. complexed calcium and 848 mg. ascorbic acid with a neutral pH of 7.0.

EXAMPLE 2

The procedure of Example 1 was repeated except that the heated solution was dried in a steam heated dryer instead of the cooling, crystallization and freeze drying steps. Assay of the product showed essentially the same results of Example 1.

EXAMPLE 3

The procedure of Example 1 was repeated except that the amount of distilled water used was reduced to 5 ml. and the heated solution was warm air dried instead of the cooling, crystallization and freeze drying steps. Assay of the product showed essentially the same results of Example 1.

EXAMPLE 4

A solution was prepared by dissolving in a nonreactive glass vessel 500 mg. calcium carbonate (USP) complexed in equal proportion with amino acids from vegetable protein, and 1000 mg. ascorbic acid (USP) of vegetable source, in 5 ml. distilled water at room temperature, as the mixture solution was stirred continuously. The aqueous mixture solution was not heated, and the product was air dried. Assay of the product showed the coordination complex conversion of compound complex calcium was approximately 100%, which showed approximately 500 mg. complexed calcium and 1000 mg. ascorbic acid.

EXAMPLE 5

A compound was prepared by completely blending 500 mg. calcium carbonate (USP) complexed in equal proportion with amino acids from vegetable protein, and 1000 mg. ascorbic acid (USP) of vegetable source. The mixture was not prepared in an aqueous solution, and, as a result, there was no drying requirement. Assay of the product showed the coordination complex conversion of compound complex calcium was approximately 100%, which showed 500 mg. complexed calcium and 1000 mg. ascorbic acid.

While compound complex calcium is intended primarily for oral ingestion, it is envisioned that it may also be injected directly into the gastrointestinal tract or administered by parenteral application. When administered orally, it may be incorporated in foodstuffs as an enrichment, or it may be used alone as a powder, crystals or liquid. Alternatively, it may be manufactured into tablets, pills or capsules with any suitable binder or carrier using any known technique. Compound complex calcium may be used in conjunction with and as an adjunct to compound complex magnesium. Whereas compound complex magnesium provides a balance for unbalanced calcium metabolism, compound complex calcium provides a balance for ionic calcium.

The conclusions reached as a result of the analysis of the clinical case studies are listed below.

1. Compound complex magnesium is absorbed more effectively than any other orally administered form of magnesium.
2. Compound complex magnesium provides more useable magnesium for use by the body than any other orally administered form of magnesium.
3. Compound complex magnesium is well tolerated, not producing gastric upset or intestinal irritability, even in those with compromised or sensitive gastrointestinal tracts.
4. Compound complex magnesium is safe, and has no deleterious side effects in those with normal renal function.
5. Compound complex magnesium can effectively balance calcium metabolism, and does so without any serum calcium sacrifice.
6. Compound complex magnesium can effectively reduce and normalize blood pressure, with a 20–30 point reduction in systolic and a 10–20 point reduction in diastolic seen in the subject.
7. Compound complex magnesium can effectively improve the blood lipid profile, increasing high density lipoproteins and lowering triglycerides.
8. Compound complex magnesium can effectively improve glycolysis, energy metabolism and insulin efficiency.
9. Compound complex magnesium can effectively improve the formation and production of cellular ATP and cyclic AMP.
10. Compound complex magnesium can effectively improve cellular function, increase cellular efficiency and reduce cellular malfunction.
11. Compound complex magnesium can effectively prevent dystrophic calcification.
12. Compound complex magnesium can effectively reduce the formation or buildup of calcified arterial plaque.
13. Compound complex magnesium can effectively reverse or lessen the progression of atherosclerosis.
14. Compound complex magnesium inhibits cardioarterial constriction and spasm.
21. Whereas adequate amounts of magnesium beneficially affect the blood, the cells, and the neuromuscular tissues of the cardiovascular system, and adequate amounts of ascorbic acid beneficially affect the blood and the blood vessel structures, when complexed magnesium and ascorbic acid are complexed together to form a compounded coordination complex of magnesium there is an exponential increase in effectiveness and when administered in effective amounts balances calcium metabolism, prevents dystrophic calcification and reduces calcified arterial plaque buildup.
22. Compound complex magnesium has a synergism of effect with other specific nutrients known to support cardiovascular health, and when administered together may allow for a lower dosage of compound complex magnesium and still receive the benefits (it has been demonstrated and noted that none of the other specific nutrients, individually or together, has the ability to balance calcium metabolism, prevent dystrophic calcification, reduce cellular malfunction or reduce calcified arterial plaque buildup without effective dosages of compound complex magnesium).
23. Compound complex magnesium has a synergism of effect with specific dietary and lifestyle modifications known to support cardiovascular health, and when incorporated with the administration of compound complex magnesium may allow for a lower dosage of compound complex magnesium and still receive the benefits (it has been demonstrated and noted that none of the other specific dietary and lifestyle modifications, individually or together, has the ability to balance calcium metabolism, prevent dystrophic calcification, reduce cellular malfunction or reduce calcified arterial plaque buildup without effective dosages of compound complex magnesium).
24. Compound complex calcium is absorbed more effectively than any other orally administered form of calcium.
25. Compound complex calcium provides more useable calcium for use by the body than any other orally administered form of calcium.
26. Compound complex calcium is well tolerated, not producing gastric upset or intestinal irritability, even in those with compromised or sensitive gastrointestinal tracts.
27. Compound complex calcium is safe, and has no deleterious side effects in those with normal renal function.
28. Compound complex calcium interacts synergistically with compound complex magnesium assisting in establishing cellular homeostasis, while ionic calcium interacts antagonistically with magnesium disrupting cellular homeostasis.
29. Compound complex calcium does not disrupt cellular function, does not contribute to cellular malfunction, and does not contribute to calcified arterial plaque buildup.
30. Compound complex calcium is not ionic and can effectively balance ionic calcium, while providing a more usable form of calcium for normal calcium functions and cellular metabolism.
31. Because of the strong interrelationship between calcium and magnesium and their functions in the human body, and as a means of making a compounded coordination complex of calcium available as an improved form of the essential mineral salt calcium that does not contribute to unbalanced calcium metabolism, dystrophic calcification, cellular malfunction or calcified arterial plaque buildup by virtue of it not being ionic calcium, there exists a need for a method of balancing ionic calcium by the making and use of compound complex calcium.

32. Compound complex calcium (which balances ionic calcium) has a natural synergism of effect with compound complex magnesium (which balances unbalanced ionic calcium metabolism), and when administered together may allow for a lower dosage of compound complex magnesium and still receive the benefits (it has been demonstrated and noted that compound complex calcium alone does not have the ability to balance calcium metabolism, prevent dystrophic calcification, reduce cellular malfunction or reduce calcified arterial plaque buildup without effective dosages of compound complex magnesium).

33. As a means of making a compounded coordination complex of inorganic minerals (including their salts, mixtures or combinations thereof), and because of the potential for enhanced intestinal absorption and cellular utilization associated with compound complex minerals, there exists a need for a standardized method of making a compound complex of inorganic minerals.

It will be apparent that while preferred embodiments of the invention have been described, various modifications and variations may be made therein without departing from the true spirit and scope of the invention. In that regard, it should be recognized that the compound complex calcium composition disclosed herein may include any pharmaceutically acceptable calcium, protein amino acids, and ascorbic acid, and may contain different proportions of each which are suitable for the purposes described herein. Therefore, the particular ratio of ingredients listed above are for purposes of example and are not intended to be a limitation of the invention. Nothing herein is intended to be a limitation of the method used and herein described to make compound complex calcium for use with other inorganic minerals, their salts or mixtures thereof.

I claim:

1. A method for reversing and reducing calcified arterial plaque buildup in the human body by administering to humans a compounded coordination complex of magnesium, said method comprising the steps of covalently binding magnesium with protein amino acids selected from the group consisting of single, dipeptide and polypeptide protein amino acids to form a coordination complex of magnesium, covalently binding said coordination complex of magnesium with ascorbic acid so as to fully form a compounded coordination complex of magnesium, and then administering said compounded coordination complex of magnesium to humans in an amount that is effective to reverse and reduce calcified arterial plaque buildup in the human body.

2. The method recited in claim 1, including the additional steps of covalently binding said magnesium with said protein amino acids in equal amounts by weight to form said coordination complex of magnesium, and then covalently binding said coordination complex of magnesium with said ascorbic acid in equal amounts by weight to fully form said compounded coordination complex of magnesium for administration to humans.

3. The method recited in claim 1, wherein said compounded coordination complex of magnesium is administered to humans orally.

4. The method recited in claim 1, wherein said compounded coordination complex of magnesium is administered to humans by parenteral application.

5. A method for improving cellular function and increasing cellular efficiency by reducing cellular malfunction in the human body by administering to humans a compounded coordination complex of magnesium, said method comprising the steps of covalently binding magnesium with protein amino acids selected from the group consisting of single, dipeptide and polypeptide protein amino acids to form a coordination complex of magnesium, covalently binding said coordination complex of magnesium with ascorbic acid so as to fully form a compounded coordination complex of magnesium, and then administering said compounded coordination complex of magnesium to humans in an amount that is effective to reduce cellular malfunction in the human body.

6. The method recited in claim 5, including the additional steps of covalently binding said magnesium with said protein amino acids in equal amounts by weight to form said coordination complex of magnesium, and then covalently binding said coordination complex of magnesium with said ascorbic acid in equal amounts by weight to fully form said compounded coordination complex of magnesium for administration to humans.

7. The method recited in claim 5, wherein said compounded coordination complex of magnesium is administered to humans orally.

8. The method recited in claim 5, wherein said compounded coordination complex of magnesium is administered to humans by parenteral application.

9. A method for balancing free unbound ionic calcium in the human body by administering to humans a compounded coordination complex of calcium, said method comprising the steps of covalently binding calcium with protein amino acids selected from the group consisting of single, dipeptide and polypeptide protein amino acids to form a coordination complex of calcium, covalently binding said coordination complex of calcium with ascorbic acid so as to fully form a compounded coordination complex of calcium, and then administering said compounded coordination complex of calcium to humans in an amount that is effective to balance free unbound ionic calcium in the human body.

10. The method recited in claim 9, including the additional steps of covalently binding said calcium with said protein amino acids in equal amounts by weight to form said coordination complex of calcium, and then covalently binding said coordination complex of calcium with said ascorbic acid in equal amounts by weight to fully form said compounded coordination complex of calcium for administration to humans.

11. The method recited in claim 9, including the additional step of selecting said calcium from a group consisting of pharmaceutical grade calcium, its salts, and mixtures thereof suitable for human consumption and application.

12. The method recited in claim 9, including the additional step of selecting said ascorbic acid from a group consisting of pharmaceutical grade ascorbic acid, its salts and mixtures thereof suitable for human consumption and application.

13. The method recited in claim 9, wherein said compounded coordination complex of calcium is administered to humans orally.

14. The method recited in claim 9, wherein said compounded coordination complex of calcium is administered to humans by parenteral application.

* * * * *